(12) United States Patent
Cole et al.

(10) Patent No.: US 6,861,250 B1
(45) Date of Patent: Mar. 1, 2005

(54) TISSUE DISSECTING BOARD ASSEMBLY

(75) Inventors: John Cole, Alpharetta, GA (US); Deron J. Singer, Shakopee, MN (US); Jason P. Porter, Mound, MN (US)

(73) Assignee: PMT Corporation, Chanhassen, MN (US)

( * ) Notice: Subject to any disclaimer, the term of this patent is extended or adjusted under 35 U.S.C. 154(b) by 0 days.

(21) Appl. No.: 10/694,368

(22) Filed: Oct. 27, 2003

Related U.S. Application Data
(60) Provisional application No. 60/421,202, filed on Oct. 25, 2002.

(51) Int. Cl.[7] ............................................... C12M 1/00
(52) U.S. Cl. ............................... 435/283.1; 435/288.3; 435/305.1; 422/99; 422/104; 606/9; 356/244; 359/397; 359/398
(58) Field of Search ............... 422/99, 104; 435/283.1, 435/288.3, 305.1; 428/409; 606/9; 356/244, 904; 359/396, 397, 398

(56) References Cited

U.S. PATENT DOCUMENTS

| | | | | |
|---|---|---|---|---|
| 4,203,231 A | * | 5/1980 | Van Note | 434/295 |
| 5,383,472 A | * | 1/1995 | Devlin et al. | 600/584 |
| 5,427,742 A | * | 6/1995 | Holland | 422/102 |
| 5,498,257 A | * | 3/1996 | Tebbetts | 606/1 |
| 5,662,661 A | * | 9/1997 | Boudjema | 606/132 |
| 6,258,327 B1 | * | 7/2001 | Tatum | 422/102 |

OTHER PUBLICATIONS

"Dishes/Dissecting", *Fischer Scientific*, 2003, p. 429, U.S.A.

"Food Quality Food Safety", *Cole–Parmer Instrument Company*, 2002, p. 574, U.S.A.

* cited by examiner

*Primary Examiner*—David A. Redding
(74) *Attorney, Agent, or Firm*—Anthony G. Eggink

(57) ABSTRACT

A tissue dissecting board assembly for use in tissue restoration and reconstruction surgeries. The assembly is constructed of an optically clear polymeric dissecting board having a plurality of cooperating cavities for holding chemical solutions and compositions required for tissue restoration and reconstruction surgeries. An illumination source is further incorporated in the dissecting board structure to provide an illuminated working area.

20 Claims, 2 Drawing Sheets

TISSUE DISSECTING BOARD ASSEMBLY

This application claims the benefit of U.S. Provisional Patent Application No. 60/421,202, filed on Oct. 25, 2002.

BACKGROUND OF THE INVENTION

This invention relates generally to a dissecting board assembly. Particularly, this invention relates to a tissue dissection board assembly for use in tissue restoration and reconstruction surgeries. More particularly, the tissue dissecting board assembly of the invention may be a single use, sterile assembly constructed and arranged for use in surgical procedures, such as in hair restoration, skin grafting, bone grafting, vascular grafting and like surgical procedures.

For example, in hair restoration surgeries for patients with hair loss, the surgery involves dissecting hair tissue flaps, for example, removed from the occipital region of the scalp, into varying sized follicle clusters for transplantation to other scalp areas. The surgical process involves the use of a cutting surface, various tissue stabilization solutions and chemical compositions and an appropriate working area.

A need exists for a surgical dissecting assembly which is constructed and arranged for various surgical procedures, such as for hair reconstruction surgeries. The tissue dissecting board assembly of the present invention satisfies that need by providing an assembly having efficient access to the necessary solutions and chemical compositions required in restoration and reconstruction surgeries and incorporating access to these solutions and chemical compositions into an illuminated work area.

SUMMARY OF THE INVENTION

The tissue dissecting board assembly of the present invention comprises an assembly preferably constructed of an optically clear polymeric structure having predetermined sizes and configurations. The assembly has a generally flat working area with a textured surface constructed and arranged for dissecting tissue. The textured surface may comprise a plurality of parallel grooves having a predetermined depth and being disposed across the working surface into the top surface of the dissecting board. The textured surface aids in controlling the movement and positioning of the tissue and minimizes or reduces the sliding of tissue.

At least one solution well is provided in the board assembly for the hydration of varying size tissue clusters or segments. The hydrating solutions may comprise water, alcohol, or a mixture thereof. One or more cavities are also provided for containing vulcanized silicone or other suitable material to aid in the adherence and dissection of tissue flaps, for example.

The polymeric structure of the board assembly is also provided with light means. For example, one or more port structures may be provided into the side or other location of the assembly to accommodate one or more fiber optic cables or other light sources to provide background illumination of the assembly working area during the dissection procedures. The light source may be an optical fiber cable, an LED or other light source which cooperate with the textured surface to diffuse light to the working area. One or more cavities are further provided in the bottom side of the assembly for receiving a vulcanized silicone or other suitable material, for example, to stabilize the board assembly during use.

An object or advantage of the invention is to provide a surgical dissecting assembly which is constructed and arranged to provide an effective and efficient illuminated working area and which provides the necessary solutions and chemical compositions required for tissue restoration and reconstruction surgeries.

These and other benefits of this invention will become clear from the following description by reference to the drawings.

DESCRIPTION OF THE PREFERRED EMBODIMENTS

This invention relates to a tissue dissection board assembly used for tissue restoration and reconstruction surgeries, which includes but is not limited to a hair follicle dissecting board assembly to treat patients with hair loss. Particularly, hair reconstruction surgery involves the dissection of hair tissue flaps which are removed from the occipital region of the scalp, and dissected into small, follicle clusters for transplant to predetermined scalp areas.

Figure 1:
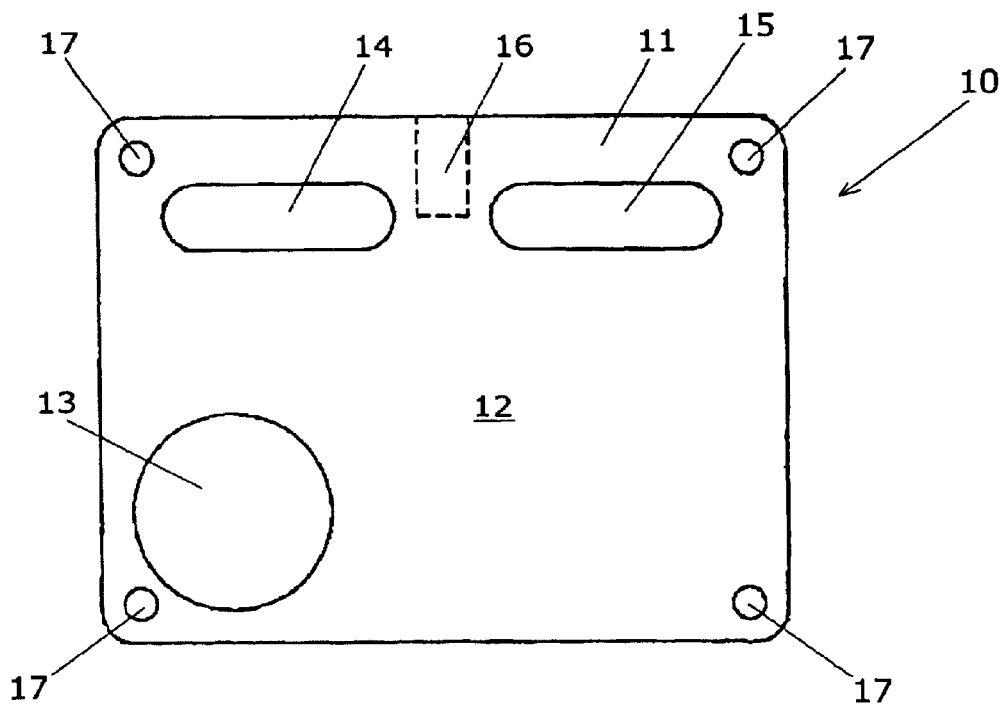
FIG. 1 is a top plan view of the tissue dissecting board assembly of the invention.
Figure 2:
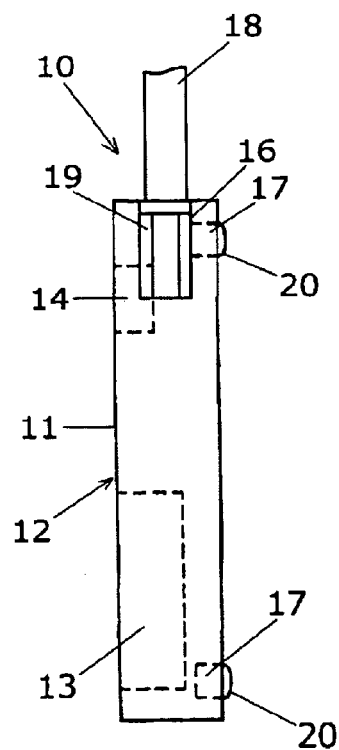
FIG. 2 is a side plan view of the tissue dissecting board assembly of FIG. 1.

Referring to FIGS. 1 and 2, the tissue dissecting board assembly 10 of the invention is shown. The dissecting board assembly 10 may be a single use, sterile device preferably constructed of an optically clear polymeric board structure 11 having specified dimensions, for example, a depth of approximately 0.787 inches, a length of approximately 5.25 inches (13.25 cm) and a width of approximately 4.0 inches (10 cm). These dimensions are exemplary for use in hair restoration surgeries, for example. Although the tissue dissecting board assembly is preferably a single use structure, it is within the purview of the invention to provide an assembly which may be used multiple times.

The dissecting board assembly 10 is further shown to have a generally flat working area for dissection of tissue and is further shown having cooperating elements. A dissecting board 11 having a textured surface 12 is provided to reduce or minimize the sliding of tissue. A solution well 13 is shown and is provided for holding a solution, i.e., water, an alcohol, or a mixture thereof, for the hydration of varying sized tissue clusters, such as small hair follicles, for example. The hydration fluid may be water, an alcohol, i.e. propylalcohol or a mixture thereof, i.e., 70% propylalcohol and 30% water. The solution well 13 is shown provided in one corner of the dissecting board 11 and which may have a diameter of approximately 1.5 inches and a depth of approximately 0.5 inches and which has been found suited for one intended purpose of the invention. Alternatively, additional solution wells may be added and may vary in dimensions to accommodate surgical requirements.

One or more cavities 14 are provided in the dissecting board 11 and are provided and filled with a vulcanized silicone or other suitable material, for example, to aid in adherence and dissection of the tissue flaps. Two cavities 14 and 15 are shown in the top of the board structure 11, and each may have a length of approximately 1.75 inches, a width of approximately 0.5 inches and a depth of approximately 0.30 inches, are provided for tissue attachment using pins, needles, or other suitable method. Alternatively, additional tissue attachment cavities can be added and which may vary in dimensions to meet the requirements of the particular surgical procedure. Although the solution well 13 and cavities 14 are preferably provided as integral with the board structure 11, separate solution and chemical containers may be provided for insertion into and use with the board structure 11.

A cavity/port 16 is further shown extending into the side of the dissecting board 11 and is provided to accommodate one or more fiber optic cables or other light sources, i.e., an LED, for background illumination during the surgical dissection procedure. For example, in FIG. 2, a light source cable 18 having a plurality of fiber optic cables 19 is shown mounted in port 15. The port 16 may have a depth of approximately 0.62 inches, and a diameter of approximately 0.39 inches which has been found suitable to receive a light source cable 18 having individual fiber optic cables 19 and to thereby illuminate or backlight the dissection board assembly 10. The utilization of a board assembly 10 constructed of an optically clear composition, such as polyvinyl chloride (PVC) or like materials and which allows the light sources in the port 16 to illuminate the assembly. The illuminated board assembly 10 provides a lighted work area particularly adapted for the surgical dissection of tissue clusters. Alternatively, additional fiber optic cavities/ports may be added and which may vary in dimensions to accommodate the size of the dissecting board 11 as well as the particular surgical procedure requirements.

Cavities 17 are further shown in the bottom side of the dissecting board 11 to receive vulcanized silicone or other suitable material, for example, and to, thereby, stabilize the board assembly 10 during use. Alternatively, other leg supports may be provided to stabilize the assembly 10 of the present invention. For example, in FIG. 2, pads 20 are shown positioned in and extending from cavities 17 to provide a stable platform for the dissecting board assembly 10.

FIGS. 1 and 2, respectively, show a top plan view and a lateral view of the tissue dissecting board assembly of the present invention. The tissue dissecting board assembly is shown to have two ports or cavities to receive a light source to thereby illuminate the assembly. The dimensions of the assembly, i.e., its length, width and height which may vary depending upon the surgical requirements and the nature of the surgery.

Figure 3:
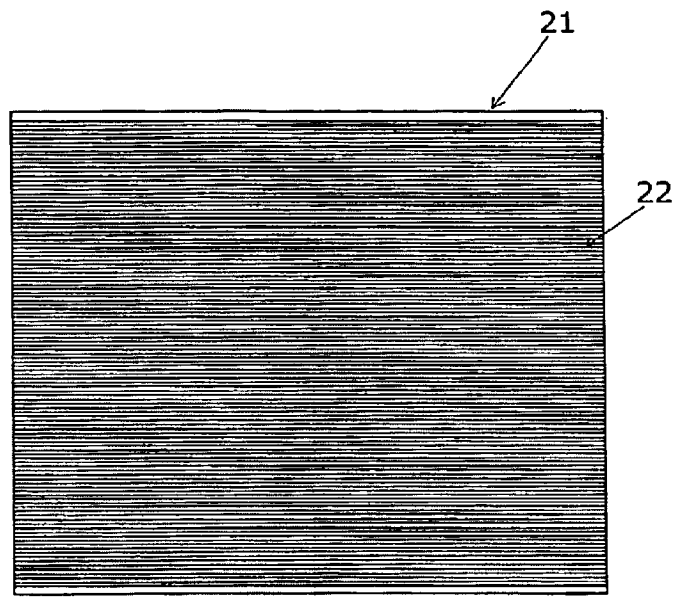
FIG. 3 is a top plan view of the texturing mold used to form the top surface texture of the tissue dissecting board of the assembly.
Figure 4:
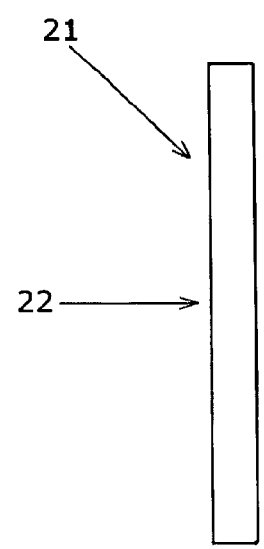
FIG. 4 is a side plan view thereof.

FIG. 3 shows a top view of a hair follicle dissecting board texturing mold 21, i.e., preferably formed of stainless steel or the like, which may be utilized to form the textured surface 12 into the top surface of the dissecting board assembly 10. The texturing mold 21 is shown to have a plurality of spaced, parallel grooves 22 and the mold structure 21 may have a length of approximately 8.5 inches, a width of approximately 7.0 inches and referring to FIG. 4 a height of approximately 0.625 inches. The dimensions of this texturing mold 21 are used to form the textured surface 12 of the 5.25 inch by 4.00 inch hair follicle dissecting board assembly 10 described above.

Figure 5:
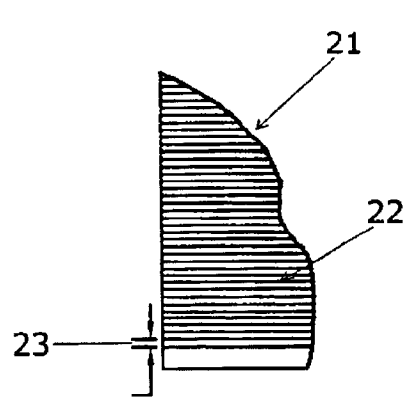
FIG. 5 is an enlarged view of a portion of the texturing mold of FIG. 5.
Figure 6:
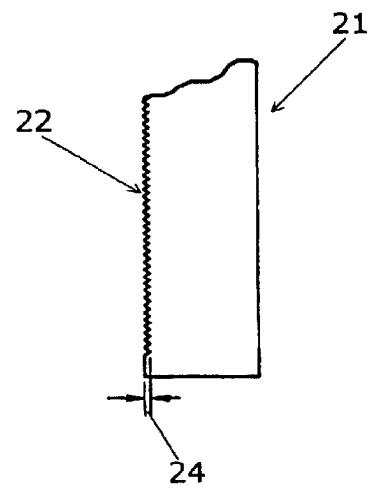
FIG. 6 is a side plan view of FIG. 7.

Referring to FIGS. 5 and 6, the texturing mold 21 is shown to have a groove spacing 23 of approximately 0.020 inches and groove depth 24 of approximately 0.030 inches. The texturing mold 21 is utilized to impart grooves into the top surface of the PVC board assembly 10 during the molding process to thereby form the texturing surface 12. As discussed, however, different textured working surfaces may be provided within the purview of the present invention.

The dimensions and structure discussed with respect to the board assembly are exemplary. The board assembly may have any dimensions and structure necessary to suit the needs of a particular tissue dissecting procedure. For example, the number of cavities, the size of the cavities and the dimensions of the working surface may be smaller or larger than the boards shown and described herein. Further, the textured surface may have a different configuration, for example, the grooves may be a cross pattern and/or the individual grooves may have a curved or curvilinear design and may have various depths for tissue control and light diffusion. The light source may also be provided within the board structure itself and may be battery powered, for example.

In summary, the tissue dissecting board assembly of the present invention provides a unitary assembly for use in tissue restoration and reconstruction surgeries. The board assembly may be a sterile, single use assembly which preferably is provided in a sealed package. The package may be a Tyvek™ pouch having a clear panel. The assembly of the invention utilizes a dissecting board constructed preferably of an optically clear polymer having rounded peripheral edges and cooperating elements as shown in FIGS. 1 and 2. Particularly, the assembly 10 is shown having a dissecting board 11 and cooperating elements in FIGS. 1 and 2, and having exemplary dimensions, as set forth above, suited for hair restoration surgeries.

As many changes are possible to the embodiments of this invention, utilizing the teachings therefor, the description above and the accompanying drawings should be interpreted in the illustrative and not the limited sense.

That which is claimed is:

1. A tissue dissecting board assembly comprising an optically clear polymeric structure having a generally flat top working surface, a bottom surface, a length, a width and a height, said polymeric structure having a peripheral side, light means disposed in said polymeric structure, said top working surface being a textured surface for tissue adherence and positioning and light diffusion, and at least one cavity extending into said top working surface of said optically clear polymeric structure.

2. The tissue dissecting board assembly of claim 1, wherein said textured surface is comprised of a plurality of parallel spaced grooves disposed across said top working surface.

3. The tissue dissecting board assembly of claim 1, wherein said at least one cavity includes first and second elongated cavities for receiving a vulcanized silicone, said first and second cavities extending in alignment along said length of said polymeric structure.

4. The tissue dissecting board assembly of claim 3, further comprising a port extending generally centrally along said length into said peripheral side of said polymeric structure and extending into said polymeric structure between said first and second elongated cavities, said port being constructed and arranged to receive said light means.

5. The tissue dissecting board assembly of claim 3, wherein said at least one cavity further includes a third cavity spacially positioned from said first and second cavities, said third cavity being a solution well for tissue hydration.

6. The tissue dissecting board assembly of claim 1, wherein said polymeric structure is comprised of polyvinyl chloride and wherein said light means comprises a fiber optic cable.

7. The tissue dissecting board assembly of claim 2, wherein said polymeric structure is a generally rectangular structure having rounded corners and wherein said bottom surface has an aperture positioned inward from each said corner and a rubber pad positioned in each said bottom aperture for stabilized said tissue dissecting board assembly during use.

8. The tissue dissecting board assembly of claim 7, wherein said polymeric structure is a disposable, single use structure having a length of approximately 8.5 inches, a width of approximately 7 inches, a thickness of approximately 0.625 inches and wherein said grooves have a width of approximately 0.02 inches and a depth of approximately 0.03 inches.

9. The tissue dissecting board assembly of claim 1, wherein said optically clear polymeric structure is in a sterile condition and wherein packaging is provided for said tissue dissecting board assembly.

10. A tissue dissecting board assembly comprising:
 a) an optically clear polymeric structure having a top working surface, a bottom surface, a length, a width and a height, said polymeric structure having a peripheral side;
 b) a port extending into said peripheral side of said polymeric structure;
 c) a light source positioned into said port;
 d) said top surface being a textured surface for tissue adherence and positioning and light diffusion;
 e) a plurality of cavities extending from said top working surface into said height of said optically clear polymeric structure; and
 f) a plurality of pads extending from said bottom surface of said polymeric structure.

11. The tissue dissecting board assembly of claim 10, wherein said plurality of cavities include first and second elongated cavities extending in alignment along said length of said polymeric structure.

12. The tissue dissecting board assembly of claim 11, wherein said port extends generally centrally along said length into said peripheral side of said polymeric structure and extends into said polymeric structure between said first and second elongated cavities.

13. The tissue dissecting board assembly of claim 11, wherein said plurality of cavities include a third cavity spacially positioned from said first and second cavities.

14. The tissue dissecting board assembly of claim 10, wherein said polymeric structure is comprised of polyvinyl chloride.

15. The tissue dissecting board assembly of claim 10, wherein said light source comprises a fiber optic cable.

16. The tissue dissecting board assembly of claim 10, wherein said plurality of cavities include a solution well for tissue hydration and a cavity containing a vulcanized silicone.

17. The tissue dissecting board assembly of claim 10, wherein said polymeric structure is a generally rectangular structure having rounded corners and wherein said bottom surface has an aperture positioned inward from each said corner for receiving said plurality of pads for stabilizing said tissue dissecting board during use.

18. The tissue dissecting board assembly of claim 10, wherein said textured surface is comprised of a plurality of parallel spaced grooves disposed across said top surface.

19. The tissue dissecting board assembly of claim 18, wherein said polymeric structure has a length of approximately 8.5 inches, a width of approximately 7 inches, a thickness of approximately 0.625 inches and wherein said grooves have a width of approximately 0.02 inches and a depth of approximately 0.03 inches.

20. A disposable, single use tissue dissecting board assembly comprising an optically clear polymeric structure having a generally flat top working surface, a bottom surface, a length, a width and a height, said polymeric structure having a peripheral side, light means disposed in said polymeric structure, said top working surface being a textured surface for tissue adherence and positioning and light diffusion, and at least one cavity extending into said top working surface of said optically clear polymeric structure, said disposable single use tissue dissecting board assembly being in a sterile condition and further being contained in packaging.

* * * * *